(12) United States Patent
Wong et al.

(10) Patent No.: US 7,009,169 B2
(45) Date of Patent: Mar. 7, 2006

(54) METHOD FOR MEASURING PARTICLE SIZE DISTRIBUTION OF A POPULATION OF PARTICLES

(75) Inventors: Joseph Chung Tak Wong, Gurnee, IL (US); Damian Neuberger, Glenview, IL (US)

(73) Assignee: Baxter International Inc., Deerfield, IL (US)

( * ) Notice: Subject to any disclaimer, the term of this patent is extended or adjusted under 35 U.S.C. 154(b) by 274 days.

(21) Appl. No.: 10/419,613

(22) Filed: Apr. 21, 2003

(65) Prior Publication Data

US 2004/0206890 A1 Oct. 21, 2004

(51) Int. Cl.
*G01V 8/00* (2006.01)
(52) U.S. Cl. .................... 250/222.2; 250/574
(58) Field of Classification Search ............ 250/222.1, 250/222.2, 574, 573, 208.1; 356/336, 338, 356/441, 442, 438
See application file for complete search history.

(56) References Cited

U.S. PATENT DOCUMENTS

| | | | |
|---|---|---|---|
| 2,525,071 A | 10/1950 | Hardy et al. ................ | 428/331 |
| 5,148,511 A * | 9/1992 | Savu et al. ................. | 385/145 |
| 6,115,575 A * | 9/2000 | Kinoshita et al. .......... | 399/286 |
| 2002/0036776 A1 | 3/2002 | Shimaoka ................... | 356/336 |
| 2002/0127278 A1 | 9/2002 | Kipp et al. ................. | 424/489 |
| 2002/0168402 A1 | 11/2002 | Kipp et al. ................. | 424/450 |
| 2002/0176935 A1 | 11/2002 | Kipp et al. ............. | 427/213.3 |
| 2003/0031719 A1 | 2/2003 | Kipp et al. ................. | 424/489 |
| 2003/0044433 A1 | 3/2003 | Werling et al. ............. | 424/400 |
| 2003/0059472 A1 | 3/2003 | Brynjelsen et al. ......... | 424/489 |
| 2003/0072807 A1 | 4/2003 | Wong et al. ................ | 424/489 |
| 2003/0077329 A1 | 4/2003 | Kipp et al. ................. | 424/489 |
| 2003/0096013 A1 | 5/2003 | Werling et al. ............. | 424/489 |
| 2003/0100568 A1 | 5/2003 | Werling et al. ......... | 514/254.07 |

OTHER PUBLICATIONS

Mroczka, Joseph, PhD., "Integral Transform Technique in Particle Sizing", J. Aerosol Sci., vol. 20, No. 8, pp. 1075-1077, 1989, printed in Great Britain.
Allen et al., "Critical Evaluation of Acute Cardiopulmonary Toxicity of Microspheres", Journal of Nuclear Medicine, vol. 19, pp. 1204-1208, 1987.
Davis et al., "Pulmonary Perfusion Imaging: Acute Toxicity and Safety Factors as Function of Particle Size", Journal of Nuclear Medicine, vol. 19, pp. 1209-1213, 1987.
Schroeder et al., "Physiological Effects of Subvisible Microspheres Administered Intravenously to Beagle Dogs", Journal of Pharmaceutical Sciences, vol. 67, No. 4, Apr. 1978, pp. 508-512.
Yokel et al., "Acute Toxicity of Latex Microspheres", Toxicology Letters, vol. 9 (1981), pp. 165-170.

* cited by examiner

*Primary Examiner*—David Porta
*Assistant Examiner*—Tony Lu
(74) *Attorney, Agent, or Firm*—Michael C. Mayo; Raymond M. Mehler (57) ABSTRACT

The present invention provides for measuring a particle size distribution of a population of particles using a light scattering particle sizing instrument having a plurality of selectable imaginary component values of the refractive index. The particles each having a particle size and the process includes the steps of: (i) providing a population of the particles, wherein the particles have a refractive index; (ii) determining a real component of the refractive index of the particles using the Becke Line Method; (iii) determining an imaginary component of the refractive index of the particles; and (iv) determining the particle size distribution of the particles by the light scattering particle sizing instrument wherein the particle size distribution is determined using the real component of the refractive index measured in step (ii) and the imaginary component of the refractive index determined in step (iii).

20 Claims, 6 Drawing Sheets

METHOD FOR MEASURING PARTICLE SIZE DISTRIBUTION OF A POPULATION OF PARTICLES

CROSS-REFERENCE TO RELATED APPLICATION:

Not Applicable.

FEDERALLY SPONSORED RESEARCH AND DEVELOPMENT

Not Applicable.

BACKGROUND OF THE INVENTION

1. Technical Field

The present invention is concerned with measuring a particle size distribution of a population of particles. Specifically, measuring a particle size distribution using a light scattering particle sizing instrument having a series of selectable imaginary component values of the refractive index.

2. Background Art

There are an ever-increasing number of organic compounds being formulated for therapeutic or diagnostic effects that are poorly soluble or insoluble in aqueous solutions. Such drugs provide challenges to delivering them by the administrative routes detailed above. Compounds that are insoluble in water can have significant benefits when formulated as a stable suspension of sub-micron particles. Accurate control of particle size is essential for safe and efficacious use of these formulations. Particles must be less than seven microns in diameter to safely pass through capillaries without causing emboli (Allen et al., 1987; Davis and Taube, 1978; Schroeder et al., 1978; Yokel et al., 1981). One solution to this problem is the production of small particles of the insoluble drug candidate and the creation of a microparticulate or nanoparticulate suspension. In this way, drugs that were previously unable to be formulated in an aqueous based system can be made suitable for intravenous administration. Suitability for intravenous administration includes small particle size (<7 $\mu$m), low toxicity (as from toxic formulation components or residual solvents), and bioavailability of the drug particles after administration.

Preparations of small particles of water insoluble drugs may also be suitable for oral, pulmonary, topical, ophthalmic, nasal, buccal, rectal, vaginal, transdermal administration, or other routes of administration. The small size of the particles improves the dissolution rate of the drug, and hence improving its bioavailability and potentially its toxicity profiles. When administered by these routes, it may be desirable to have particle size in the range of 5 to 100 $\mu$m, depending on the route of administration, formulation, solubility, and bioavailability of the drug. For example, for intravenous administration, it is desirable to have a particle size of less than about 7 $\mu$m. For pulmonary administration, the particles are preferably less than about 10 $\mu$m in size.

One common method to measure the particle size of these particles is image analysis using microscopy. However, existing image analysis methods can only provide a two-dimensional image (i.e., surface areas of the particles).

Another common method for particle size determination is to use a light scattering instrument, which measures the average particle size of a population of particles as well as the distribution of the particle size of the particles. The light scattering method reports a three-dimensional (i.e., volume) equivalent sphere diameter. One example of a commonly used light scattering instrument is the Horiba LA-920 laser light diffraction instrument. The light scattering method is particularly adapted to measuring particle size and particle size distributions of the small particles in a dispersion.

In order to measure the particle size and particle size distribution of these small particles by a light scattering instrument, two parameters are required for input into the instrument, the real component and the imaginary component of the refractive index of the particles, as expressed by the following equation:

$$RI = n - ik$$

where RI is the refractive index of the particles, n is the real component (also known as the real index) of the refractive index, which is the ratio of the velocity of light in a vacuum to the velocity of light in the particle, and k is the imaginary component (also known as the imaginary or complex index) of the refractive index, which is the extinction coefficient of the particle, and $i = (-1)^{1/2}$. The imaginary component of the extinction coefficient k is the reduction of transmission of optical radiation in the particle caused by absorption and scattering of the light. It is expressed mathematically in the following equation:

$$k = (\lambda/4\pi)\alpha$$

where $\alpha$ is the absorption coefficient and $\lambda$ is the wavelength of light. The absorption coefficient ($\alpha$) is the reciprocal of the distance that the light will penetrate the particle and be reduced to 1/e of its intensity before striking the particle. Transparent particles allow more penetration of light than opaque particles. Therefore, transparent particles have low absorption coefficient while opaque particles have high absorption coefficient.

Figure 1A:
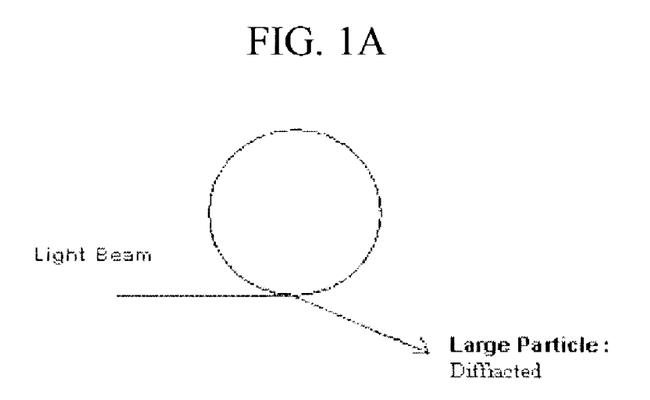
FIG. 1A is a schematic diagram of a light beam striking a large particle.
Figure 1B:
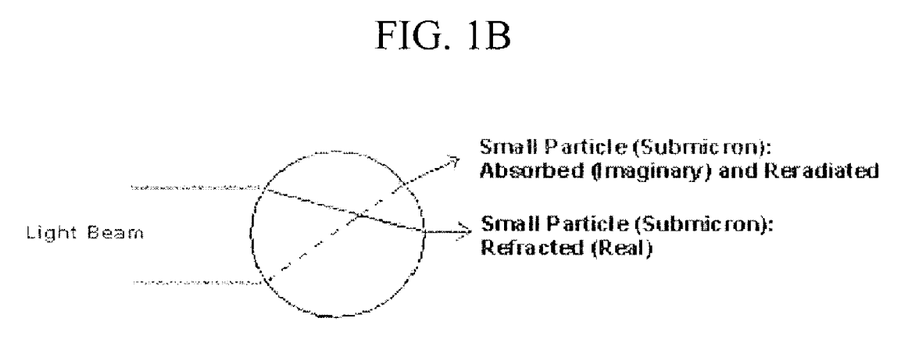
FIG. 1B is a schematic diagram of a light beam striking a small particle illustrating the imaginary and real components of the refractive index.

The real and the imaginary components of the refractive index are further illustrated in FIGS. 1A and 1B. As shown in FIG. 1A, when a light beam strikes a particle, it is predominantly diffracted if the particle is large relative to the wavelength of the incident light (e.g. particle size of several microns and the wavelengths for Horiba LA-920 of 405 nm and 633 nm). Particle size index values are less significant in the measurement of size of these large particles. However, if the particles are small (e.g., submicron size) relative to the wavelength of the incident lights of, for example, 405 nm or 633 nm, the light can be absorbed and reradiated (FIG. 1B). The light striking the small particle is also scattered, mainly by refraction. In these small particles, the absorbed and reradiated light represents the imaginary component of the refractive index and the refracted light represents the real component of the refractive index (FIG. 1B). Particle size index values become very significant in the measurement of the size of these small particles.

The real component of the refractive index for a small particle can be measured using methods such as the Becke Line Method, or it can be obtained from published tables. However, there is no known method to measure the imaginary component portion of the refractive index for input into a light scattering particle sizing instrument. A value is selected by the user, for example, based on an estimate of the degree of transparency or opacity of the material being analyzed with one selectable imaginary component corresponding to completely opaque particles, another selectable imaginary component corresponding to translucent particles, another selectable imaginary component corresponding to particles that are most transparent but might have a rough surface or a non-spherical shape and another selectable imaginary component corresponding to transparent, spherical particles. For example, the options available for the refractive input on a laser light scattering instrument are 0.00i (completely transparent particles), 0.01i, 0.10i, and 1.0i (some what opaque to opaque particles). The manufacturer recommends that if the particles are not completely transparent or opaque, either 0.01i or 0.1i should probably be selected.

Additionally, light scattering particle sizing instruments calculate particle size and particle size distribution based on the assumption that all particles are spherical. The real components of the refractive index values are most important in particle size distribution measurements if the particles are (i) small, (ii) spherical, and (iii) transparent. If the characteristics of the particles deviate from any or all of these conditions, the real components of the refractive index are less important and the selection of higher imaginary components is recommended.

The imaginary component is most important when the size of the particles being measured is close to the wavelengths of the light source (e.g., the wavelengths for Horiba LA-920 are 405 nm and 633 nm), for example when measuring ultra-fine sub-micron particles (less than one micron). A need exists to accurately determine the selectable imaginary component of the refractive index for small sized particles.

The present invention discloses a method to determine the correct value of imaginary component of the particles which can be used to more accurately determine the particle size and particle size distribution, particularly the 100 percentile particle size distribution. The method is most applicable to particles of less than 1 µm.

SUMMARY OF THE INVENTION

The present invention provides a method for measuring particle size and particle size distribution of a population of particles using a light scattering particle sizing instrument. The method includes the steps of: (1) providing a population of the particles; (2) determining the real component of the refractive index of the particles; (3) determining the imaginary component of the refractive index of the particles; and (4) determining the particle size distribution of the particles by the light scattering particle sizing instrument with the input of the values of the real component of the refractive index and the imaginary component of the refractive index determined.

In a preferred embodiment, the real component of the particles is determined by the Becke Line Method.

In another preferred embodiment, the imaginary component of the refractive index is determined by a method including the steps of using a series of imaginary component value of the refractive index to determine the particle size distributions of the particles. The corresponding 100 percentile values for the population of particles can be determined for each of the value of the imaginary component of the refractive index. By determining the largest particle size volume using a method other than the light scattering method and matching the result from the light scattering instrument, the correct imaginary component value of the refractive index can be determined.

These and other aspects and attributes of the present invention will be discussed with reference to the following drawings and accompanying specification.

DETAILED DESCRIPTION OF THE INVENTION

While this invention is susceptible of embodiment in many different forms, there is shown in the drawing, and will be described herein in detail, specific embodiments thereof with the understanding that the present disclosure is to be considered as an exemplification of the principles of the invention and is not intended to limit the invention to the specific embodiments illustrated.

The present invention provides a method for measuring a particle size distribution of a population of particles using a light scattering particle sizing instrument. The method includes the steps of: (1) providing a population of the particles; (2) determining the real component of the refractive index of the particles; (3) determining the imaginary component of the refractive index of the particles; and (4) determining the particle size distribution of the particles by the light scattering particle sizing instrument with the input of the values of the real component of the refractive index and the imaginary component of the refractive index determined.

The particle size distribution measurement of the present invention begins with providing a population of particles. The particles for use in the present invention may be any amorphous particle, any crystalline particle or any other suitable particle. The particle may be an organic or an inorganic compound. An organic compound for use in the process of this invention might be, but is not limited to a pharmaceutically active compound, which can be selected from therapeutic agents, diagnostic agents, cosmetics, nutritional supplements, and pesticides.

The population of particles of the present invention can be prepared by any of the methods known in the art. The methods include, but are not limited to microprecipitation methods or emulsion methods. Examples of these methods are disclosed in co-pending and commonly assigned U.S. patent applications Ser. Nos. 60/258,160; 09/874,799; 09/874,637; 09/874,499; 09/964,273; 10/035,821, 60/347,548; 10/021,692; 10/183,035; 10/213,352; 10/246,802; 10/270,268; 10/270,267, and 10/390,333 which are incorporated by reference herein and are made a part hereof.

The next step of the present invention is determining the real component of the refractive index of the population of provided particles. The real component of the refractive index of the material of the particles can be obtained from published tables. Alternatively, it can be measured. One commonly used method to measure the real component is the Becke Line Method. The Becke Line Method is a microscopic technique that determines the real component of the refractive index of a solid by immersing small particles of the solid in liquids of known refractive indices on microscope slides. When the slides are viewed with a microscope and the focus is raised, a faint line of light called the Becke Line will enter the medium of higher refractive index, be it the solid or the liquid. By repeating the process systematically with liquids of incrementally different refractive indices, the refractive index of the solid will be found to equal the refractive index of one liquid or to be between two liquids.

After determining the real component, the imaginary component of the refractive index of the particles is determined. The light scattering instrument of the present invention includes a series of selectable imaginary component values of the refractive index. Each selectable imaginary component value corresponds to the degree of transparency or opacity of the material being analyzed. For example, one selectable imaginary component corresponds to completely opaque particles, another selectable imaginary component corresponds to translucent particles, another selectable imaginary component corresponds to particles that are most transparent but might have a rough surface or a non-spherical shape and another selectable imaginary component corresponds to transparent, spherical particles. In one embodiment, the light scattering instrument of the present invention is a laser diffraction particle size analyzer.

In a preferred embodiment, the imaginary component of the refractive index is determined by a method including the steps of using the series of imaginary component value of the refractive index provided by the instrument to determine the particle size distributions of the particles. The corresponding 100 percentile values for the population of particles can be determined for each of the values of the imaginary component of the refractive index. By determining the largest particle size volume using a method other than the light scattering method and matching the result from the light scattering instrument, the correct imaginary component value of the refractive index can be determined. In a preferred embodiment, the non-light scattering method begins with providing a subpopulation of the particles from the population of the particles. In one embodiment, the subpopulation is provided by filtering a suspension of the particles to retain the subpopulation on a filter. In this embodiment, the subpopulation is selected to consist of particles with size larger than the retention rating of the filter. The suspension can be an aqueous medium or a non-aqueous medium compatible with the filter. The filtered particles of the subpopulation are preferably separated from each other on the filter with no overlap or little or no touching of the particles on the filter.

From the filtered subpopulation, the largest particle is selected. The largest particle can be selected by any methods known in the art. The methods include, but are not limited to selecting the largest particle by inspection with a microscope, such as, but not limited to, an optical microscope, a scanning electron microscope, a laser scanning microscope, a confocal microscope or a scanning probe microscope.

After selecting the largest particle(s) from the subpopulation, the particle's size is determined by a method which is not by a light scattering particle sizing instrument. In a preferred embodiment, the particle size is determined by image analysis using a microscope. In another preferred embodiment, the particle size is determined by manual measurement using a microscope. The microscope used to determine the selected particle size may be, but is not limited to, an optical microscope, a scanning electron microscope, a laser scanning microscope, a confocal microscope or a scanning probe microscope. A preferred non-light scattering method to determine particle size is disclosed in the co-pending and commonly assigned U.S. patent application Ser. No. 10/419,612, which is incorporated by reference herein and made a part hereof.

After determining the selected particle's size by a non-light scattering method described above, the particle size distribution of the population of the particles is determined using the laser light diffraction instrument for each available values of the selectable imaginary components of the refractive index from the instrument. For each of the value of the selectable imaginary component, a particle size representing the 100 percentile distribution is obtained. The selected 100 percentile particle size is then compared to the particle size of the largest particle(s) in the subpopulation determined by the non-light scattering method described earlier. The selected imaginary component of the refractive index that provides the particle size that is closest to the largest particle size determined by the non-light scattering method is then selected as the imaginary component of the refractive index for the present invention. This imaginary component value can be selected for the instrument in analyzing the particle size and particle size distribution of other batches of similar particles, particularly particles prepared with similar methods and with similar chemical and physical characteristics.

EXAMPLES

Example 1

Measuring the Particle Size Distribution for a Population of Itraconazole Particles The particle size distribution of a suspension of submicron size itraconazole particles was determined using the Horiba LA-920 laser diffraction particle size analyzer manufactured by Horiba Instruments Inc., (17671 Armstrong Ave, Irvine Calif., 92614). The Horiba LA-920 provides for three selectable imaginary component values of the refractive index. They are 0.00i (for completely transparent particles), 0.01i, and 0.1i (for somewhat opaque particles). Moreover, the Horiba LA-920 provides the distribution of the particle populations in the range of 0.020 to 2000 $\mu$m.

The real component of the refractive index for itraconazole particles was determined using the Becke Line Method.

Figure 2:
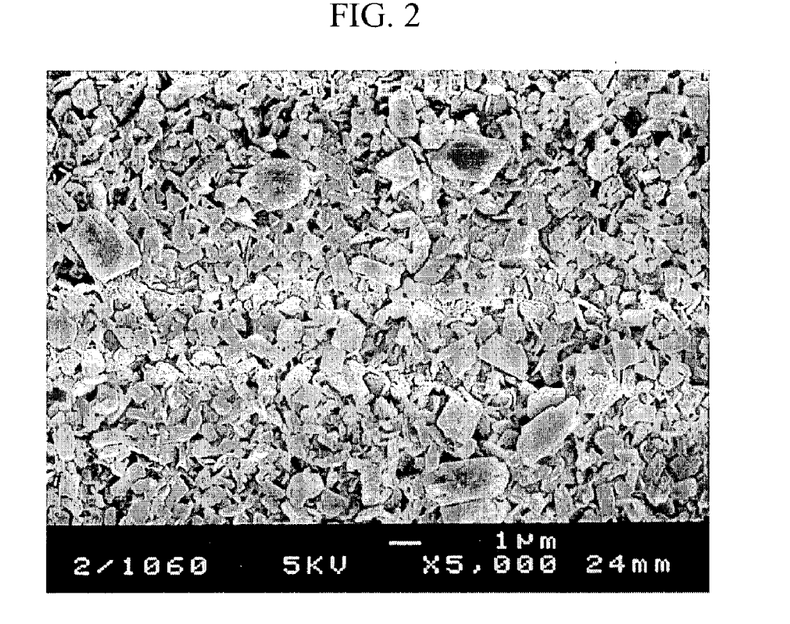
FIG. 2 is a scanning electron photomicrograph of a population of itraconazole particles of Example 1 showing a wide range of particle sizes.
Figure 3:
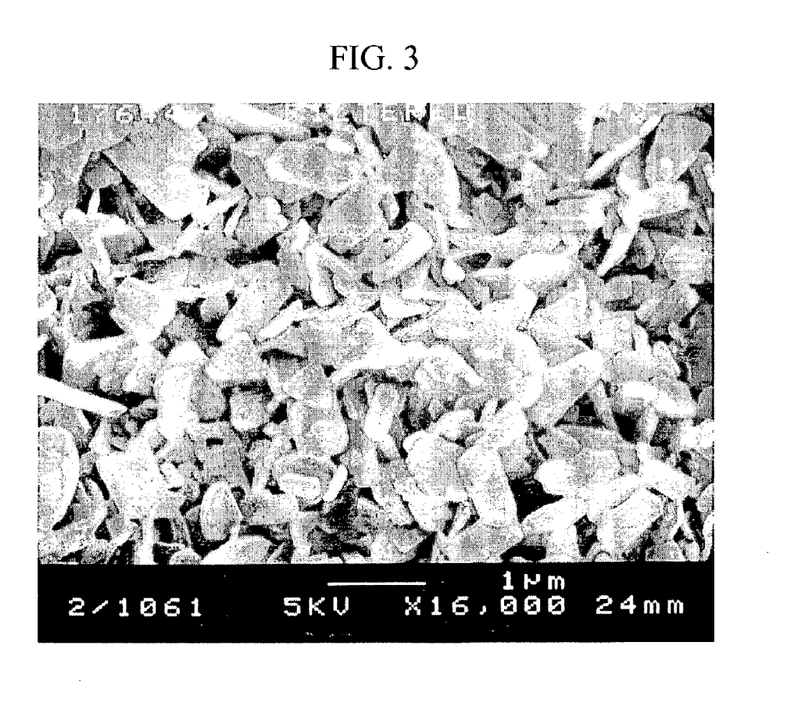
FIG. 3 is a scanning electron photomicrograph of the population of itraconazole particles of Example 1 showing the smaller particle sizes.
Figure 4:
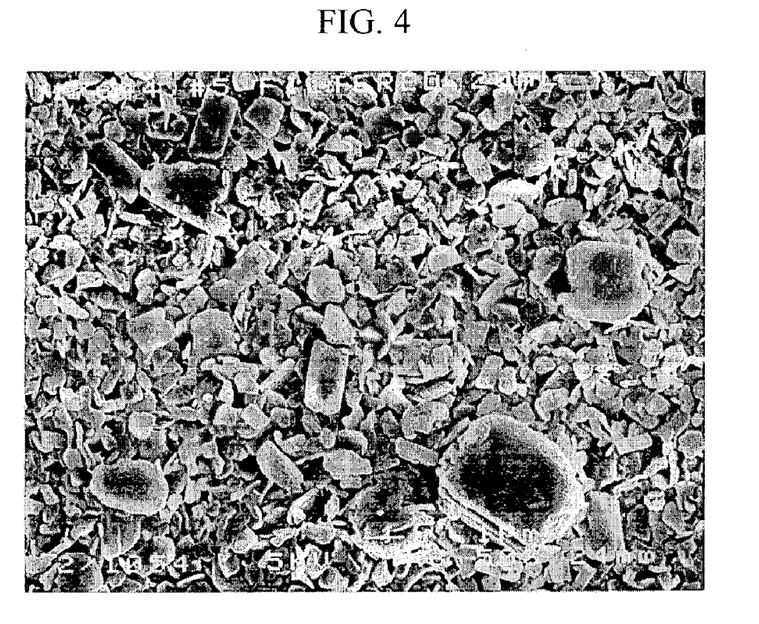
FIG. 4 is a scanning electron photomicrograph of the population of itraconazole particles of Example 1 showing the larger particle sizes.

The imaginary component of the refractive index for the itraconazole particles was then determined. The method begins with preparing a dilute suspension of itraconazole particles. The dilute suspension was filtered onto a 0.2 μm retention anodized aluminum membrane filter to provide a subpopulation of the itraconazole particles. Digital images of the particles were recorded with a high resolution JEOL 6300F field emission, low voltage scanning electron microscope (FE-LVSEM) using a MCP secondary electron detector. FIGS. 2, 3 and 4 show scanning electron photomicrographs of a dispersion sample showing a wide range of itraconazole particle sizes recorded at 5,000× magnification.

Figure 5:
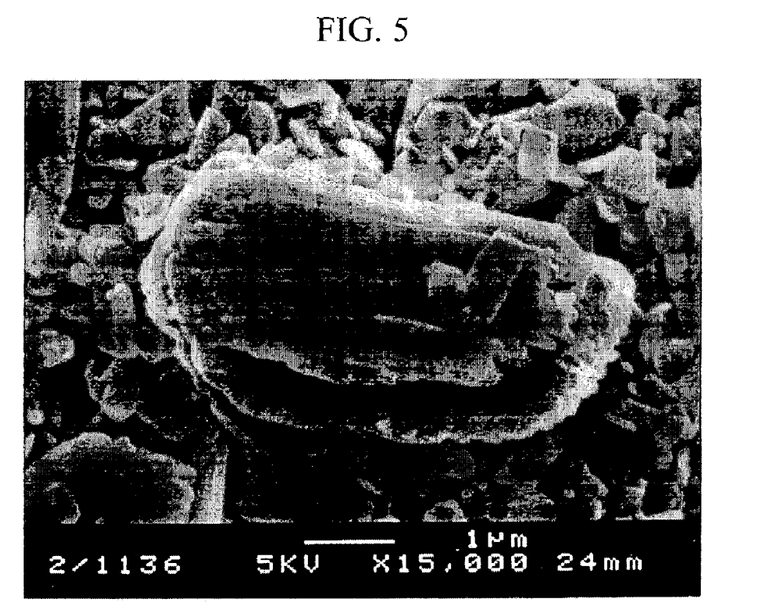
FIG. 5 is a scanning electron photomicrograph of particle #1 from Example 1 shown normal to the optical axis.
Figure 6:
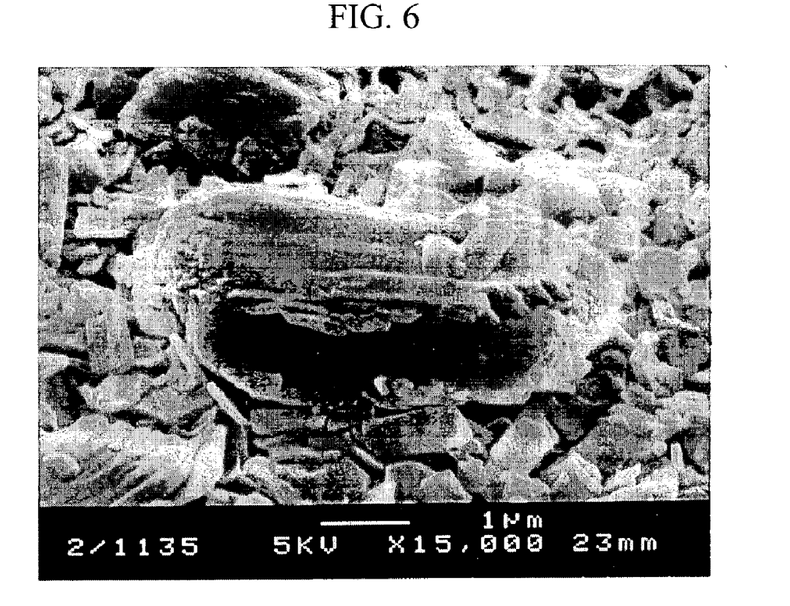
FIG. 6 is a scanning electron photomicrograph of particle #1 from Example 1 shown tilted 45° to the normal plane.
Figure 7:
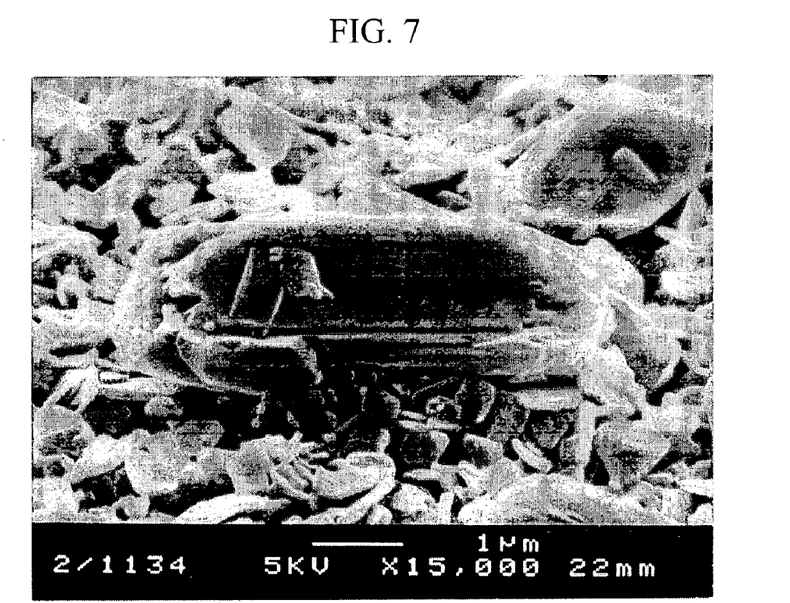
FIG. 7 is a scanning electron photomicrograph of particle #1 from Example 1 shown rotated 180° and tilted 45° to the normal plane.
Figure 8:
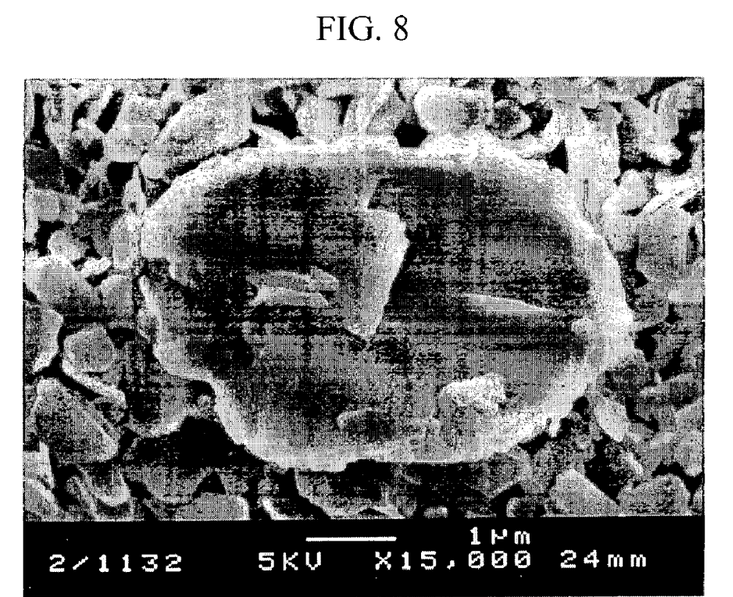
FIG. 8 is a scanning electron photomicrograph of particle #2 from Example 1 shown normal to the optical axis.
Figure 9:
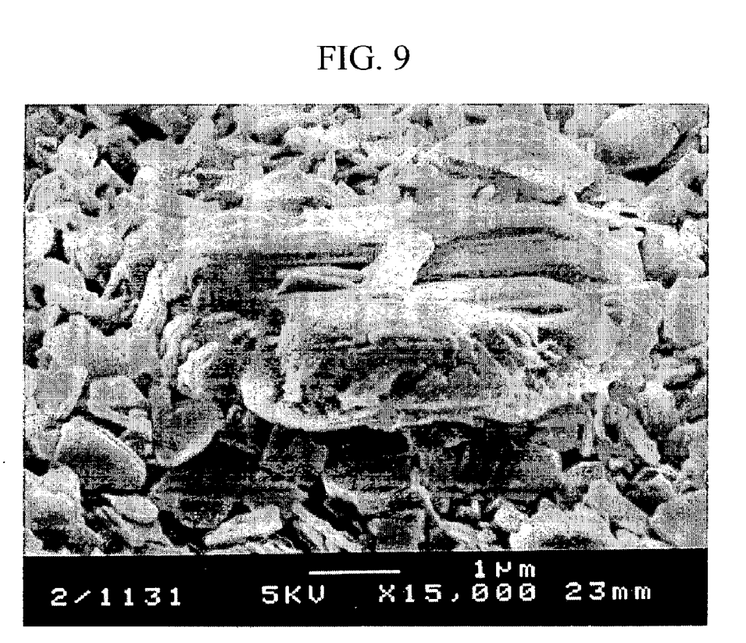
FIG. 9 is a scanning electron photomicrograph of particle #2 from Example 1 shown tilted 45° to the normal plane.
Figure 10:
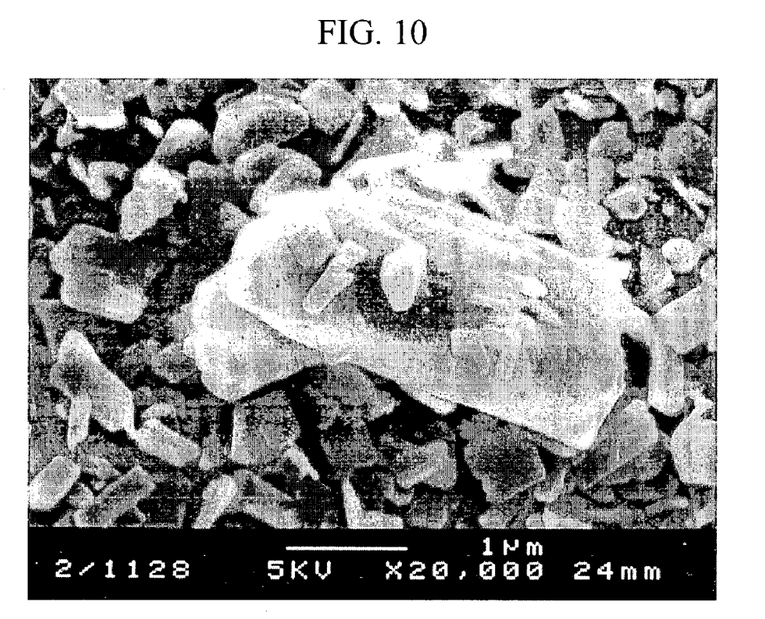
FIG. 10 is a scanning electron photomicrograph of particle #3 from Example 1 shown normal to the optical axis.
Figure 11:
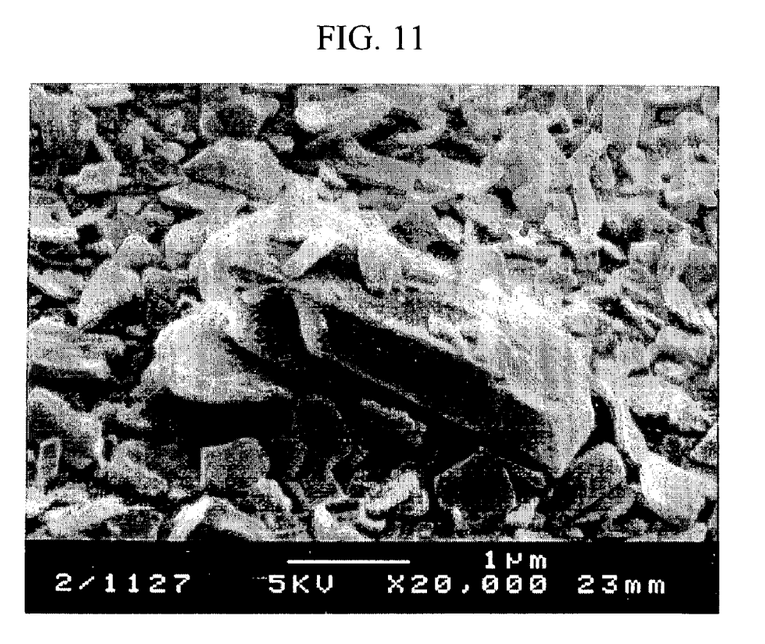
FIG. 11 is a scanning electron photomicrograph of particle #3 from Example 1 shown tilted 450 to the normal plane.

The provided subpopulation was inspected with the scanning electron microscope and the three largest particles (particles #1, #2 and #3) were selected. Selected particle #1 is shown in FIGS. 5 to 7; selected particle #2 is shown in FIGS. 8 and 9 and selected particle #3 is shown in FIGS. 10 and 11. For each of the selected particles, the size of the particle as the sphere equivalent diameter was determined by the image analysis method disclosed in the copending and commonly assigned U.S. patent application Ser. No. 10/419,612.

Table 1 shows the particle sizes determined by the above image analysis method for the three particles selected.

TABLE 1

Particle Volume Values and the Associated Equivalent Sphere Diameters

| Particle Number | Particle Volume ($\mu m^3$) | Equivalent Sphere Diameter D ($\mu m$) |
| --- | --- | --- |
| #1 | 14.8750 | 3.05 |
| #2 | 25.7018 | 3.66 |
| #3 | 4.1923 | 2.001 |

After determining the particle size for the selected particles, the particle size distribution of the population of the particles using the Horiba LA-920 was determined using each of the three selectable imaginary component values. Table 2 is the measured particle size distribution values for the suspension of itraconazole particles using the various selectable imaginary component values available on the Horiba LA-920. The use of refractive index input of 122a010i generated the highest 99 percentile and 100 percentile values of particle size distribution. The 100 percentile value was 2.973. This value is in close agreement with the equivalent sphere diameter of 3.66 μm obtained by the image analysis method in Table 1. The 99 percentile and 100 percentile values generated using the inputs of 122a001i and 122a000i were approximately the same. The 100 percentile levels of about 0.9 μm generated with these two inputs were lower than the values generated using the input of 122a010i. In addition, the mean values generated regardless of the Horiba refractive index input were approximately 0.4 μm for the sample.

TABLE 2

Measured Particle Size Distribution of Itraconazole Particles With Various Input Values of the Imaginary Component of the Refractive Index

| Horiba LA-920 Refractive Index Input | Measured Particle Size Distribution | | |
| --- | --- | --- | --- |
| | Mean ($\mu m$) | 99% ($\mu m$) | 100% ($\mu m$) |
| 122a010i | 0.4301 | 1.688 | 2.973 |
| 122a001i | 0.3587 | 0.657 | 0.877 |
| 122a000i | 0.3603 | 0.656 | 0.877 |

From this comparison, it was determined that the imaginary component value that corresponds to the selection of 122a010i provided the particle size that was closest to the particle size determined by image analysis as shown in Table 1. This imaginary component value can be selected for the instrument in analyzing the particle size and particle size distribution of other batches of similar particles, particularly particles prepared with similar methods and with similar chemical and physical characteristics.

While specific embodiments have been illustrated and described, numerous modifications come to mind without departing from the spirit of the invention and the scope of protection is only limited by the scope of the accompanying claims.

The invention is claimed as follows:

1. A method for measuring a particle size distribution of a population of particles using a light scattering particle sizing instrument having a plurality of selectable imaginary component values of the refractive index, and the method comprising the steps of:
    (i) providing a population of the particles;
    (ii) determining a real component of the refractive index of the particles;
    (iii) determining an imaginary component of the refractive index of the particles, wherein the method of determining the imaginary component of the refractive index of the particles comprises the steps of:
        (a) providing a subpopulation of the particles from the population of the particles;
        (b) selecting the largest particle from the subpopulation;
        (c) determining the particle size of the particle by a method which is not by a light scattering particle sizing instrument;
        (d) determining the particle size distribution of the population of the particles using a light scattering particle sizing instrument for each of the selectable imaginary component values of the refractive index;
        (e) selecting a particle size representing the particle size distribution of the population;
        (f) comparing the particle size selected in step (e) and particle size determined in step (c); and
        (g) selecting the imaginary component value of the refractive index that provides the particle size in step (e) that is closest to the particle size of the particle determined using the method in step (c); and
    iv) determining the particle size distribution of the particles by the light scattering particle sizing instrument wherein the particle size distribution is determined using the real component of the refractive index measured in step (ii) and the imaginary component of the refractive index determined in step (iii).

2. The method of claim 1 wherein the method of determining the real component of the refractive index is by the Becke Line Method.

3. A method for measuring a particle size distribution of a population of particles using a light scattering particle sizing instrument having a plurality of selectable imaginary component values of the refractive index, and the method comprising the steps of: (i) providing a population of the particles; (ii) determining a real component of the refractive index of the particles; (iii) determining an imaginary component of the refractive index of the particles, wherein the method of determining the imaginary component of the refractive index of the particles comprises the steps of:
    (a) providing a subpopulation of the particles from the population of the particles;

(b) selecting the largest particle from the subpopulation;

(c) determining the particle size of the particle by a method which is not by a light scattering particle sizing instrument;

(d) determining the particle size distribution of the population of the particles using a laser light diffraction instrument for each of the selectable imaginary component values of the refractive index;

(e) selecting a particle size representing the 100 percentile of the particle size distribution of the population;

(f) comparing the particle size selected in step (e) and particle size determined in step (c); and (g) selecting the imaginary component value of the refractive index that provides the particle size in step (e) that is closest to the particle size of the particle determined using the method in step (c); and (iv) determining the particle size distribution of the particles by the light scattering particle sizing instrument wherein the particle size distribution is determined using the real component of the refractive index measured in step (ii) and the imaginary component of the refractive index determined in step (iii).

4. The method of claim 3 wherein the method for providing the subpopulation of the particles is by filtering a suspension of the particles to retain the subpopulation of particles on a filter.

5. The method of claim 3 wherein the method of step (ii) is by inspection with a microscope.

6. The method of claim 5, wherein the microscope is selected from the group consisting of an optical microscope, a scanning electron microscope, a laser scanning microscope, a confocal microscope and a scanning probe microscope.

7. The method of claim 3 wherein the method of step (c) is by image analysis or manual measurement.

8. The method of claim 7, wherein the method comprises using a microscope.

9. The method of claim 8, wherein the microscope is selected from the group consisting of an optical microscope, a scanning electron microscope, a laser scanning microscope, a confocal microscope and a scanning probe microscope.

10. The method of claim 1 wherein the light scattering particle sizing instrument is a laser light diffraction instrument.

11. The method of claim 1 wherein the particles are less than about 1 $\mu$m.

12. The method of claim 1 wherein the particle size distribution is a 100% distribution.

13. The method of claim 3 wherein the method of determining the real component of the refractive index is by the Becke Line Method.

14. The method of claim 1 wherein the method for providing the subpopulation of the particles is by filtering a suspension of the particles to retain the subpopulation of particles on a filter.

15. The method of claim 1 wherein the method of step (ii) is by inspection with a microscope.

16. The method of claim 15, wherein the microscope is selected from the group consisting of an optical microscope, a scanning electron microscope, a laser scanning microscope, a confocal microscope and a scanning probe microscope.

17. The method of claim 1 wherein the method of step (iii) is by image analysis or manual measurement.

18. The method of claim 17, wherein the method comprises using a microscope.

19. The method of claim 18, wherein the microscope is selected from the group consisting of an optical microscope, a scanning electron microscope, a laser scanning microscope, a confocal microscope and a scanning probe microscope.

20. The method of claim 3 wherein the particles are less than about 1 $\mu$m.

* * * * *